United States Patent
Ci

(10) Patent No.: US 10,596,215 B2
(45) Date of Patent: Mar. 24, 2020

(54) CHINESE HERBAL ORAL PASTE FOR CONDITIONING DAMPNESS-HEAT CONSTITUTION AND PROCESSING METHOD THEREOF

(71) Applicant: Zhonghua Ci, Beijing (CN)

(72) Inventor: Zhonghua Ci, Beijing (CN)

(*) Notice: Subject to any disclaimer, the term of this patent is extended or adjusted under 35 U.S.C. 154(b) by 0 days.

(21) Appl. No.: 15/969,490

(22) Filed: May 2, 2018

(65) Prior Publication Data

US 2019/0192605 A1 Jun. 27, 2019

(30) Foreign Application Priority Data

Dec. 26, 2017 (CN) .......................... 2017 1 1429340

(51) Int. Cl.

| | | |
|---|---|---|
| A61K 36/00 | (2006.01) |
| A61K 36/752 | (2006.01) |
| A61K 9/00 | (2006.01) |
| A61K 36/64 | (2006.01) |
| A61K 36/906 | (2006.01) |
| A61K 36/36 | (2006.01) |
| A61K 36/232 | (2006.01) |
| A61K 36/9064 | (2006.01) |
| A61K 36/282 | (2006.01) |
| A61K 36/48 | (2006.01) |
| A61K 36/634 | (2006.01) |
| A61K 36/8966 | (2006.01) |
| A61K 36/42 | (2006.01) |
| A61K 36/534 | (2006.01) |
| A61K 36/28 | (2006.01) |
| A61K 36/88 | (2006.01) |
| A61K 36/756 | (2006.01) |
| A61K 36/70 | (2006.01) |
| A61K 36/076 | (2006.01) |
| A61K 36/8945 | (2006.01) |
| A61K 36/736 | (2006.01) |
| A61K 36/8994 | (2006.01) |
| A61K 36/899 | (2006.01) |
| A61K 36/815 | (2006.01) |
| A61K 36/484 | (2006.01) |
| A61K 36/536 | (2006.01) |
| A61K 36/605 | (2006.01) |
| A61K 36/63 | (2006.01) |
| A61K 36/539 | (2006.01) |
| A61K 9/06 | (2006.01) |
| A61K 35/50 | (2015.01) |
| A61K 47/26 | (2006.01) |

(52) U.S. Cl.
CPC .......... *A61K 36/752* (2013.01); *A61K 9/0053* (2013.01); *A61K 9/0056* (2013.01); *A61K 9/06* (2013.01); *A61K 35/50* (2013.01); *A61K 36/076* (2013.01); *A61K 36/232* (2013.01); *A61K 36/28* (2013.01); *A61K 36/282* (2013.01); *A61K 36/36* (2013.01); *A61K 36/42* (2013.01); *A61K 36/48* (2013.01); *A61K 36/484* (2013.01); *A61K 36/534* (2013.01); *A61K 36/536* (2013.01); *A61K 36/539* (2013.01); *A61K 36/605* (2013.01); *A61K 36/63* (2013.01); *A61K 36/634* (2013.01); *A61K 36/64* (2013.01); *A61K 36/70* (2013.01); *A61K 36/736* (2013.01); *A61K 36/756* (2013.01); *A61K 36/815* (2013.01); *A61K 36/88* (2013.01); *A61K 36/899* (2013.01); *A61K 36/8945* (2013.01); *A61K 36/8966* (2013.01); *A61K 36/8994* (2013.01); *A61K 36/906* (2013.01); *A61K 36/9064* (2013.01); *A61K 47/26* (2013.01)

(58) Field of Classification Search
None
See application file for complete search history.

*Primary Examiner* — Qiuwen Mi

(74) *Attorney, Agent, or Firm* — Novick, Kim & Lee, PLLC; Allen Xue

(57) ABSTRACT

The present application discloses a Chinese herbal oral paste for conditioning dampness-heat constitution. The Chinese herbal oral paste includes the following components: baical skullcap root, unprocessed rehmannia root, plantain seed, purslane herb, angelica, cardamon fruit, virgate wormwood herb, rice beans, weeping forsythia capsule, thunberg fritillary bulb, Chinese waxgourd peel, mint, dried tangerine peel, prepared atractylodes rhizome, waxgourd seed, common anemarrhena rhizome, amur cork-tree, golden buckwheat rhizome, fuling, Chinese yam, bitter apricot seed, coix seed, bamboo leaf, Chinese wolfberry root-bark, ural licorice root tip, common selfheal fruit-spike, white mulberry root-bark, ash bark, tortoise-plastron gelatin, turtle shell gelatin, and xylitol. The Chinese herbal oral paste of the present disclosure has a higher drug concentration and good taste, is particularly suitable for health preserving in winter and conditioning the dampness-heat constitution, will not create negative effects to the human body at all, and can achieve certain efficacy of strengthening physical health.

20 Claims, 1 Drawing Sheet

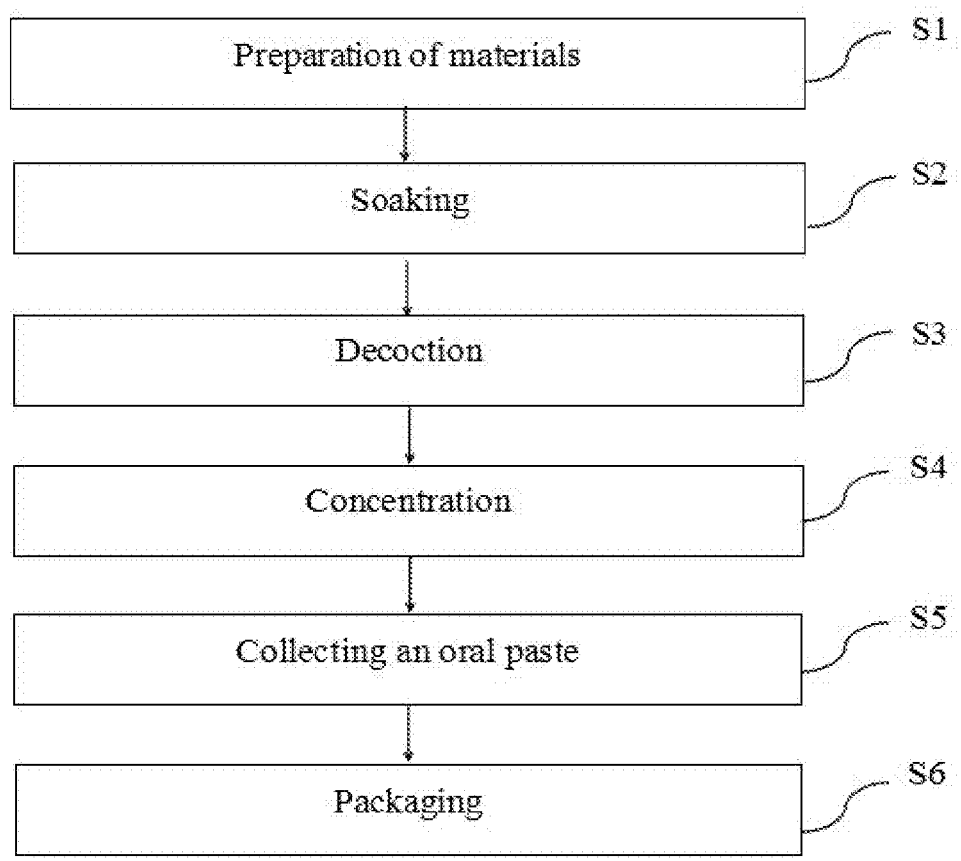

CHINESE HERBAL ORAL PASTE FOR CONDITIONING DAMPNESS-HEAT CONSTITUTION AND PROCESSING METHOD THEREOF

TECHNICAL FIELD

The present disclosure relates to the field of health foods, and particularly to a Chinese herbal oral paste for conditioning dampness-heat constitution and a processing method therefor.

BACKGROUND

In *Classification and Determination of Constitution in Traditional Chinese Medicine*, the China Association of Chinese Medicine classifies body constitutions of the human body into nine types, including yin-yang harmony constitution, yang deficiency constitution, yin deficiency constitution, qi deficiency constitution, phlegm-dampness constitution, dampness-heat constitution, qi depression constitution, blood stasis constitution, and allergic constitution, most of which belong to sub-healthy states.

The so-called dampness, which is commonly referred to as water-dampness, includes exogenous dampness and endogenous dampness. The exogenous dampness is caused by invasion of exogenous water-dampness into the human body as a result of humid climate, wading, exposure to rain or dampness of living room. The endogenous dampness is a pathological product and often relates to digestive function. It is believed by traditional Chinese medicine that the spleen has the function of "transportation and transformation of water-dampness". In case of indigestion due to weakness, overeating or eating too much oily food or sweets, the spleen cannot perform the function of transportation and transformation of water-dampness, leading to "internal retention of water-dampness". Moreover, people with spleen deficiency tend to incur invasion of exogenous dampness, and the functioning of spleen and stomach is often frustrated by exogenous dampness, leading to endogeny of dampness. Thus there is both independent and related relationship between the exogenous dampness and the functioning of spleen and stomach. The so-called heat is a kind of symptom caused by heat. In the case of dampness-heat, heat and dampness coexist. Because dampness and heat invades simultaneously the human body due to the muggy weather in summer and autumn, or the dampness is retained for a long time to transform into heat, or the dampness is transformed by the "yang-heat constitution" "from yang into heat", the simultaneous presence of dampness and heat is very common.

Such sub-healthy constitution as dampness-heat constitution belongs to chronic diseases and has a relatively long disease course, and requires a long-term medication and gradual conditioning, in order to achieve the effects of removing heat to eliminate dampness. The drug forms commonly used in the traditional Chinese medicine are decoctions and Chinese patent medicine such as pills and the like. Decoctions usually have relatively good efficacy, but the administration thereof is complicated, and the taste thereof is poor. If the decoctions need to be prepared for a long time, it is difficult for a patient to keep taking the decoctions. Moreover, the efficacy of the pills is relatively poor.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and susceptibility to diseases. It is believed in the traditional Chinese medicine that since the human beings live in the natural world, physiological functions of the human body usually change with seasons, that is, "correspondence between man and nature". Winter is the season when the human body "stores energies", thus appropriate nourishment can enhance the constitution, ward off diseases and strengthen the body, and prolong life, that is, conditioning in winter or nourishing in winter commonly mentioned in the traditional Chinese medicine. For the sub-healthy population with dampness-heat constitution, a solid oral paste with a higher drug concentration and good taste, and being convenient to carry more meets requirements of modern people.

SUMMARY

A main object of the present disclosure is to provide a Chinese herbal nourishing product suitable for conditioning in winter so as to treat dampness-heat constitution.

In order to achieve the above object, according to one aspect of the present disclosure, there is provided a Chinese herbal oral paste for conditioning dampness-heat constitution.

The Chinese herbal oral paste for conditioning dampness-heat constitution according to the present disclosure includes the following components in parts by weight: 5-15 parts of baical skullcap root, 5-15 parts of unprocessed rehmannia root, 4-16 parts of plantain seed, 12-28 parts of purslane herb, 3-17 parts of angelica, 1-5 parts of cardamon fruit, 5-19 parts of virgate wormwood herb, 9-21 parts of rice beans, 5-15 parts of weeping forsythia capsule, 5-16 parts of thunberg fritillary bulb, 10-30 parts of Chinese waxgourd peel, 3-9 parts of mint, 2-9 parts of dried tangerine peel, 7-19 parts of prepared atractylodes rhizome, 8-22 parts of waxgourd seed, 2-9 parts of common anemarrhena rhizome, 4-16 parts of amur cork-tree, 8-23 parts of golden buckwheat rhizome, 7-18 parts of fuling, 6-18 parts of Chinese yam, 5-15 parts of bitter apricot seed, 11-27 parts of coix seed, 5-16 parts of bamboo leaf, 8-20 parts of Chinese wolfberry root-bark, 2-9 parts of ural licorice root tip, 9-22 parts of common selfheal fruit-spike, 6-18 parts of white mulberry root-bark, 5-17 parts of ash bark, 7-25 parts of tortoise-plastron gelatin, 15-35 parts of turtle shell gelatin, and 20-30 parts of xylitol.

Furthermore, the Chinese herbal oral paste for conditioning dampness-heat constitution according to the present disclosure includes the following components in parts by weight: 7-13 parts of baical skullcap root, 7-13 parts of unprocessed rehmannia root, 7-13 parts of plantain seed, 16-24 parts of purslane herb, 7-13 parts of angelica, 2-4 parts of cardamon fruit, 9-15 parts of virgate wormwood herb, 12-18 parts of rice beans, 7-13 parts of weeping forsythia capsule, 7-13 parts of thunberg fritillary bulb, 15-25 parts of Chinese waxgourd peel, 5-7 parts of mint, 5-7 parts of dried tangerine peel, 9-15 parts of prepared atractylodes rhizome, 11-19 parts of waxgourd seed, 4-7 parts of common anemarrhena rhizome, 7-13 parts of amur cork-tree, 12-18 parts of golden buckwheat rhizome, 9-15 parts of fuling, 9-15 parts of Chinese yam, 7-13 parts of bitter apricot seed, 15-25 parts of coix seed, 7-13 parts of bamboo leaf, 12-18 parts of Chinese wolfberry root-bark, 4-8 parts of ural licorice root tip, 12-18 parts of common selfheal fruit-spike, 9-15 parts of white mulberry root-bark, 7-13 parts of ash bark, 10-20 parts of tortoise-plastron gelatin, 20-30 parts of turtle shell gelatin, and 25-35 parts of xylitol.

Furthermore, the Chinese herbal oral paste for conditioning dampness-heat constitution according to the present disclosure includes the following components in parts by weight: 10 parts of baical skullcap root, 10 parts of unprocessed rehmannia root, 10 parts of plantain seed, 20 parts of purslane herb, 10 parts of angelica, 3 parts of cardamon fruit, 12 parts of virgate wormwood herb, 15 parts of rice beans, 10 parts of weeping forsythia capsule, 10 parts of thunberg fritillary bulb, 20 parts of Chinese waxgourd peel, 6 parts of mint, 6 parts of dried tangerine peel, 12 parts of prepared atractylodes rhizome, 15 parts of waxgourd seed, 6 parts of common anemarrhena rhizome, 10 parts of amur cork-tree, 15 parts of golden buckwheat rhizome, 12 parts of fuling, 12 parts of Chinese yam, 10 parts of bitter apricot seed, 20 parts of coix seed, 10 parts of bamboo leaf, 15 parts of Chinese wolfberry root-bark, 6 parts of ural licorice root tip, 15 parts of common selfheal fruit-spike, 10 parts of white mulberry root-bark, 10 parts of ash bark, 15 parts of tortoise-plastron gelatin, 25 parts of turtle shell gelatin, and 30 parts of xylitol.

In order to achieve the above object, according to the other aspect of the present disclosure, there is a processing method for a Chinese herbal oral paste for conditioning dampness-heat constitution.

The processing method for a Chinese herbal oral paste for conditioning dampness-heat constitution according to the present disclosure includes the following steps in sequence: preparation of materials, soaking, decoction, concentration, and collecting an oral paste.

Furthermore, the step of preparation of materials is: measuring raw materials of formula ratio according to composition of the Chinese herbal oral paste, and washing raw materials, except turtle shell gelatin, tortoise-plastron gelatin, and xylitol, for subsequent use.

Furthermore, the soaking step is: soaking the cleaned raw materials with 8-10 folds of water for 8-15 h, with the water over the raw materials by 10-20 cm.

Furthermore, the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining decoction juice with the squeezed juice, followed by static settlement for 2 h, and filtering, to obtain a supernatant liquid for subsequent use.

Furthermore, the concentration step is: boiling and skimming the supernatant liquid resulted in the decoction step, followed by stirring while decocting and concentrating with low heat, until the drug liquid does not disperse when being dropped on paper, to obtain a vegetarian paste.

Furthermore, the step of collecting an oral paste is: pouring xylitol, melted turtle shell gelatin and tortoise-plastron gelatin into the vegetarian paste respectively, stirring them continuously with a shovel while cooking them slowly with low heat, until the juice coagulates into beads when dropped into clear water and does not disperse, and canning the resulted oral paste.

The melting step is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

The Chinese herbal oral paste of the present disclosure has a higher drug concentration and good taste, is particularly suitable for health preserving in winter and conditioning the dampness-heat constitution, will not create negative effects or harm to the human body at all, and is capable of achieving certain efficacy of strengthening physical health.

BRIEF DESCRIPTION OF THE DRAWINGS

The accompanying drawing, which constitutes a part of the present application, is used to provide a further understanding of the present disclosure, so that other features, objects, and advantages of the present application become more obvious. The illustrative drawings for embodiments of the present disclosure and the description thereof are used to explain the present disclosure, rather than constitute an improper limitation on the present disclosure. In the drawing, FIG. 1 is a flow chart of a processing technology for a Chinese herbal oral paste of an embodiment of the present disclosure.

DETAILED DESCRIPTION OF THE EMBODIMENTS

In order to enable a person skilled in the art to better understand the solutions of the present application, the technical solutions of the embodiments of the present disclosure will be described clearly and completely below with reference to the accompanying drawing of the embodiments of the present application. Apparently, the embodiments described are merely for some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below in combination with the embodiments.

A Chinese herbal oral paste for conditioning dampness-heat constitution of the present disclosure includes the following components: baical skullcap root, unprocessed rehmannia root, plantain seed, purslane herb, angelica, cardamon fruit, virgate wormwood herb, rice beans, weeping forsythia capsule, thunberg fritillary bulb, Chinese waxgourd peel, mint, dried tangerine peel, prepared atractylodes rhizome, waxgourd seed, common anemarrhena rhizome, amur cork-tree, golden buckwheat rhizome, fuling, Chinese yam, bitter apricot seed, coix seed, bamboo leaf, Chinese wolfberry root-bark, ural licorice root tip, common selfheal fruit-spike, white mulberry root-bark, ash bark, tortoise-plastron gelatin, turtle shell gelatin, and xylitol.

Baical skullcap root is bitter in flavor and cold in nature, acts on heart, lung, gallbladder, and large intestine, discharges excess fire, eliminates dampness-heat, stops bleeding, prevents miscarriage, and is used for high fever and polydipsia, cough due to the lung heat, dampness-heat diarrhea, jaundice, heat strangury, hematemesis, bleeding from five sense organs or subcutaneous tissue, metrorrhagia, metrostaxis, sore red swollen eyes, fetal upset, and carbuncle boils and scabies.

Unprocessed rehmannia root is sweet in flavor and cold in nature, acts on heart, liver, and kidney, removes heat, generates body fluid, nourishes yin, replenishes blood, and is used for yin-deficiency heat, consumptive thirst, hematemesis, bleeding from five sense organs or subcutaneous tissue, metrorrhagia, irregular menstruation, fetal upset, and yin-injury constipation.

Plantain seed is sweet in flavor and cold in nature, acts on kidney and bladder, alleviates water retention, removes heat, improves eyesight, eliminates phlegm, and is used for urinary obstruction, stranguria with turbid discharge, leucorrhoea disease, hematuria, summer-heat diarrhea, cough with excessive phlegm, dampness arthralgia, and bloodshot eye and blurred vision.

Purslane herb is sour in flavor and cold in nature, acts on liver and large intestine, clears away heat and toxic materials, cools blood for hemostasis, relieves dysentery; and is used for heat toxicity and bloody dysentery, abscess and furuncle, eczema, erysipelas, snake and insect bites, hematochezia, hemorrhoidal bleeding, metrorrhagia and hematochezia.

Angelica is sweet and acrid in flavor and warm in nature, acts on liver, heart, and spleen, replenishes blood and invigorates the circulation of blood, regulates menstruation and relieves pain, relaxes bowel, and is used for blood-deficiency etiolation, vertigo and palpitation, irregular menstruation, amenorrhea and dysmenorrhea, deficiency-cold stomachache, rheumatic arthralgia, traumatic injury, ulcer and skin and external diseases, and constipation due to intestinal dryness. Alcohol-boiled angelica is used for amenorrhea and dysmenorrhea, rheumatic arthralgia, and traumatic injury.

Cardamon fruit is acrid in flavor and warm in nature, acts on spleen and stomach, resolves dampness and promotes the circulation of qi, warms the middle energizer and arrests vomiting, stimulates appetite and promotes digestion, and is used for dampness obstruction and qi stagnation, incoordination between spleen and stomach, abdominal fullness and distention, poor appetite, beginning of damp-warm syndrome, oppression in the chest without hunger, stomach cold vomiting, and indigestion.

Virgate wormwood herb is bitter and acrid in flavor and slightly cold in nature, acts on spleen, stomach, liver, and gallbladder, clears away heat and promotes diuresis, removes jaundice, and is used for jaundice, difficult urination, eczema and itching, infectious jaundice hepatitis and so on. According to pharmacological research, it has the effects of benefiting gallbladder, protecting liver functions, cooling down, resisting inflammation, reducing blood fat, reducing blood pressure, expanding coronary artery and so on.

Rice beans are sweet and sour in flavor and neutral in nature, act on heart and small intestine, alleviate water retention and relieve swelling, clear away toxic materials and discharge pus, and are used for edema distention, beriberi edema, jaundice and dark urine, wind-dampness pyretic arthralgia, carbuncle, and intestinal carbuncle and stomachache.

Weeping forsythia capsule is bitter in flavor and cool in nature, acts on heart, liver, and gallbladder, removes heat, clears away toxic materials, removes stasis, relieves swelling, and is used for warm heat, erysipelas, macula, carbuncle, scrofula, and dribbling urination and anuresis.

Thunberg fritillary bulb is bitter in flavor and cold in nature, acts on lung and heart, removes heat to eliminate phlegm and relieve cough, clears away toxic matters to remove stasis and resolves carbuncle, and is used for cough due to wind-heat, pyrophlegm cough, pulmonary abscess, acute mastitis, crewels, and carbuncle.

Chinese waxgourd peel is sweet in flavor and cool in nature, acts on spleen and small intestine, promotes urination and relieves swelling, and is used for edema distention, difficult urination, summer-heat thirst, and scanty dark urine.

Mint is acrid in flavor and cool in nature, acts on lung and liver, dispels wind and heat, clears and disinhibits the head and eyes, relieves sore throat and promotes eruption, soothes the liver and promotes the circulation of qi, and is used for common cold due to wind-heat, headache, swollen sore throat, dyspepsia and flatulence, aphtha, toothache, furuncle, urticarial, beginning of warm diseases, rubella pruritus, liver depression and qi stagnation, chest distress and hypochondriac pain.

Dried tangerine peel is bitter and acrid in flavor and warm in nature, acts on lung and spleen, regulates qi and tonifies spleen, dries dampness and resolves phlegm, and is used for abdominal fullness and distention, reduced appetite and vomiting, and cough with excessive phlegm.

Prepared atractylodes rhizome is acrid and bitter in flavor and warm in nature, acts on spleen, stomach, and liver, dries dampness and tonifies spleen, dispels wind to eliminate cold, improves eyesight, and is used for dampness retention in middle jiao, abdominal fullness and distention, diarrhea, edema, beriberi paralysis, arthralgia due to wind-dampness, common cold due to wind-cold, nyctalopia, and faint and obscure eyesight.

Waxgourd seed is sweet in flavor and cool in nature, acts on lung, large intestine, and bladder, moistens lung, resolves phlegm, resolves carbuncle, alleviates water retention, and is used for cough due to phlegm-heat, pulmonary abscess, intestinal carbuncle, gonorrhea, edema, dermatophytosis, haemorrhoids, and brandy nose and face.

Common anemarrhena rhizome is bitter in flavor and cold in nature, acts on lung, stomach, and kidney, removes heat and purges pathogenic fire, nourishes yin and moistens dryness, and is used for pyreticosis polydipsia, dry cough due to the lung heat, steaming bone hectic fever, internal-heat consumptive thirst, and constipation due to intestinal dryness.

Amur cork-tree is bitter in flavor and cold in nature, acts on kidney and bladder, removes heat and dries dampness, purges pathogenic fire and clears hectic heat, clears away toxic matters and treats furuncles, and is used for dampness-heat dysentery, jaundice and dark urine, leucorrhoea disease and vulval pruritus, astringent pain, beriberi paralysis, steaming bone consumptive fever, night sweating, gonobolia, toxic swelling of skin and external diseases, and eczema.

Golden buckwheat rhizome is sour and bitter in flavor and cold in nature, acts on lung, stomach, and liver, removes heat and toxic matters, invigorates blood circulation to resolve carbuncle, dispels wind and dampness, and is used for pulmonary abscess, lung-heat cough and asthma, swollen sore throat, dysentery, arthralgia syndrome due to wind-dampness, traumatic injury, carbuncle, and snake and insect bites.

Fuling is sweet and light in flavor and neutral in nature, acts on heart, lung, spleen, and kidney, alleviates water retention and clears dampness, tonifies spleen, calms the mind, and is used for edema and scanty urine, phlegm and fluid retention and dizziness and palpitation, reduced spleen-deficiency appetite, loose stool and diarrhea, uneasiness, and palpitation to insomnia.

Chinese yam is sweet in flavor, neutral in nature, and non-toxic, acts on spleen, lung, and kidney, strengthens spleen and stomach, nourishes lung qi, tonifies kidney essence, nourishes physical health, renders good hearing and eyesight and delays senility upon long administration, and is used for reduced spleen-deficiency appetite, loose stool diarrhea, lung-deficiency asthma, gonobolia and frequent urination, and yin-deficiency consumptive thirst.

Bitter apricot seed is bitter in flavor and slightly warm in nature, acts on lung and large intestine, relieves cough and asthma, lubricates intestine to relax bowel, and is used for cough and dyspnea, and constipation due to intestinal dryness.

Coix seed is sweet and light in flavor and cool in nature, acts on spleen, stomach, and lung, alleviates water retention and clears dampness, tonifies spleen and cures diarrhea, eliminates arthralgia syndromes, discharges pus, clears away toxic matters and removes stasis, and is used for edema, beriberi, difficult urination, spleen-deficiency diarrhea, dampness arthralgia muscular constriction, pulmonary abscess, intestinal carbuncle, excrescence, and cancerous protuberance.

Bamboo leaf is sweet and light in flavor and cold in nature, acts on heart, lung, and stomach, removes heat to relieve restlessness, promotes the secretion of body fluid, promotes urination, and is used for pyreticosis polydipsia, infantile convulsion, choking cough, and haematemesis, scanty dark urine, aphthous stomatitis and tongue boil.

Chinese wolfberry root-bark is sweet in flavor and cold in nature, acts on lung, liver, and kidney, removes heat, cools blood, and is used for consumptive hectic fever and night sweating, lung-heat cough and asthma, hematemesis, bleeding from five sense organs or subcutaneous tissue, stranguria, consumptive thirst, hypertension, carbuncle, and malignant sore.

Ural licorice root tip is sweet in flavor and cold in nature, acts on heart, small intestine, and bladder, discharges fire and removes toxic matters, induces diuresis for treating stranguria, and is used for heat strangury, short and scanty urine, pain in penis, and heat accumulation in chest.

Common selfheal fruit-spike is acrid and bitter in flavor and cold in nature, acts on liver and gallbladder, removes heat and purges pathogenic fire, improves eyesight, removes stasis and swelling, and is used for sore red swollen eyes, headache and dizziness, eye pain at night, scrofula, thyroid tumor, acute mastitis swelling pain.

White mulberry root-bark is sweet and acrid in flavor and cold in nature, acts on lung and spleen, purges the lung of pathogenic fire and relieves asthma, alleviates water retention and relieves swelling, and is used for lung-heat cough and asthma with phlegm, water retention stagnating in lung, distention and syndrome characterized by dyspnea, edema, beriberi, and difficult urination.

Ash bark is bitter and astringent in flavor and cold in nature, acts on liver, gallbladder, and large intestine, removes heat to dry dampness, promotes astriction and relieves dysentery, arrests leucorrhoea, improves eyesight, and is used for warm-heat diarrhea, leukorrhea with reddish discharge, sore red swollen eyes, and cataract.

Tortoise-plastron gelatin is sweet and salty in flavor and neutral in nature, nourishes yin, replenishes blood, stops bleeding, and is used for yin-deficiency blood depletion, consumptive heat and steaming bone, hematemesis, bleeding from five sense organs or subcutaneous tissue, dysphoria with smothery sensation and palpitation, kidney-deficiency backache, impotent feet and knees, metrorrhagia and metrostaxis, and leucorrhoea.

Turtle shell gelatin is sweet and salty in flavor and slightly cold in nature, acts on liver, lung, and kidney, nourishes yin and allays fever, resolves hard lump, and is used for yin-deficiency hectic fever, consumptive disease and hemoptysis, chronic malaria, malaria with abdominal mass, hemorrhoids gall, and blood-deficiency amenorrhea.

The general manifestations of dampness-heat are as follows: heavy limbs, obvious fever in the afternoon which cannot be relieved by sweating; greasy tongue coating and rapid pulse. Depending on the different parts of body where dampness-heat is present, the specific manifestations varies. For example, eczema or malignant boil occurs in the case that dampness-heat is in skin and flesh; local swelling and pain occurs in the case of the joints, tendon and vessel. But the commonly said dampness-heat often refers to dampness-heat into internal organs, especially dampness-heat in the spleen and stomach, which is manifested as epigastric oppression and fullness of the abdomen, nausea and anorexia, loose stool, short and red urine, and soft pulse. Other dampness-heat includes, such as, dampness-heat in liver and gallbladder which is manifested as liver swelling pain, mouth with bitter taste and poor appetite, skin and eyes yellowing, alternate fever and cold, wiry pulse; dampness-heat in bladder which is manifested as frequent urination, urgent urination, astringent urination and urination pain, yellow and turbid urine; dampness-heat in intestinum which is manifested as abdominal pain and diarrhea and even tenesmus, bloody purulent stool, burning pain in anus, and thirst. Since the symptoms of the dampness-heat constitution have a variety of manifestation, therapy should be divided into eliminating dampness and clearing heat-fire. The Chinese herbal oral paste of the present disclosure addresses the causes of diseases of dampness-heat with predominant heat of people with the dampness-heat constitution through the efficacies of removing heat and toxic matters, regulating the middle energizer to descend qi, and tonifying spleen and promoting diuresis of various drugs. With the multiple types of drug materials of large dosages, efficacies of the various drug materials generate a synergistic effect, with the functions of eliminating dampness and heat, and the dampness-heat constitution can be corrected, so that people are vigorous with strong resistibility, and the occurrence of diseases is avoided. With the correction for such constitution, it is more targeted and will not create side effects, without harm to the human body at all, and can achieve certain efficacy of strengthening the body.

As shown in FIG. 1, the processing method for the Chinese herbal oral paste for conditioning dampness-heat constitution of the present disclosure includes the following steps in sequence: preparation of materials, soaking, decoction, concentration, collecting an oral paste, and finally packaging. For specific operations of respective steps, reference can be made to various embodiments of the present disclosure.

Embodiment 1:

A Chinese herbal oral paste for conditioning dampness-heat constitution includes the following components in parts by weight: 5 parts of baical skullcap root, 5 parts of unprocessed rehmannia root, 4 parts of plantain seed, 12 parts of purslane herb, 3 parts of angelica, 1 parts of cardamon fruit, 5 parts of virgate wormwood herb, 9 parts of rice beans, 5 parts of weeping forsythia capsule, 5 parts of thunberg fritillary bulb, 10 parts of Chinese waxgourd peel, 3 parts of mint, 2 parts of dried tangerine peel, 7 parts of prepared atractylodes rhizome, 8 parts of waxgourd seed, 2 parts of common anemarrhena rhizome, 4 parts of amur cork-tree, 8 parts of golden buckwheat rhizome, 7 parts of fuling, 6 parts of Chinese yam, 5 parts of bitter apricot seed, 11 parts of coix seed, 5 parts of bamboo leaf, 8 parts of Chinese wolfberry root-bark, 2 parts of ural licorice root tip, 9 parts of common selfheal fruit-spike, 6 parts of white mulberry root-bark, 5 parts of ash bark, 7 parts of tortoise-plastron gelatin, 15 parts of turtle shell gelatin, and 20 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, and xylitol, for subsequent use;

soaking: soaking the cleaned raw materials with 8 folds of water for 8 h, with the water over the raw materials by 10 cm;

decoction: decocting the soaked drug materials over flame, firstly boiling the drug materials with high heat to sufficiently expand, then boiling the drug materials with low heat for 1 hour of decoction, then filtering drug juice with gauze, then soaking filtered dregs of decoction with clear water and decocting the soaked dregs of decoction with low heat for 1 hour, thus repeating 4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin and tortoise-plastron gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 2:

A Chinese herbal oral paste for conditioning dampness-heat constitution includes the following components in parts by weight: 15 parts of baical skullcap root, 15 parts of unprocessed rehmannia root, 16 parts of plantain seed, 28 parts of purslane herb, 17 parts of angelica, 5 parts of cardamon fruit, 19 parts of virgate wormwood herb, 21 parts of rice beans, 15 parts of weeping forsythia capsule, 16 parts of thunberg fritillary bulb, 30 parts of Chinese waxgourd peel, 9 parts of mint, 9 parts of dried tangerine peel, 19 parts of prepared atractylodes rhizome, 22 parts of waxgourd seed, 9 parts of common anemarrhena rhizome, 16 parts of amur cork-tree, 23 parts of golden buckwheat rhizome, 18 parts of fuling, 18 parts of Chinese yam, 15 parts of bitter apricot seed, 27 parts of coix seed, 16 parts of bamboo leaf, 20 parts of Chinese wolfberry root-bark, 9 parts of ural licorice root tip, 22 parts of common selfheal fruit-spike, 18 parts of white mulberry root-bark, 17 parts of ash bark, 25 parts of tortoise-plastron gelatin, 35 parts of turtle shell gelatin, and 30 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, and xylitol, for subsequent use;

soaking: soaking the cleaned raw materials with 10 folds of water for 15 h, with the water over the raw materials by 20 cm;

decoction: decocting the soaked drug materials over flame, firstly boiling the drug materials with high heat to sufficiently expand, then boiling the drug materials with low heat for 2 hours of decoction, then filtering drug juice with gauze, then soaking filtered dregs of decoction with clear water and decocting the soaked dregs of decoction with low heat for 1 hour, thus repeating 2 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin and tortoise-plastron gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 3:

A Chinese herbal oral paste for conditioning dampness-heat constitution includes the following components in parts by weight: 7 parts of baical skullcap root, 7 parts of unprocessed rehmannia root, 7 parts of plantain seed, 16 parts of purslane herb, 7 parts of angelica, 2 parts of cardamon fruit, 9parts of virgate wormwood herb, 12 parts of rice beans, 7 parts of weeping forsythia capsule, 7 parts of thunberg fritillary bulb, 15 parts of Chinese waxgourd peel, 5 parts of mint, 5 parts of dried tangerine peel, 9 parts of prepared atractylodes rhizome, 11 parts of waxgourd seed, 4 parts of common anemarrhena rhizome, 7 parts of amur cork-tree, 12 parts of golden buckwheat rhizome, 9 parts of fuling, 9 parts of Chinese yam, 7 parts of bitter apricot seed, 15 parts of coix seed, 7 parts of bamboo leaf, 12 parts of Chinese wolfberry root-bark, 4 parts of ural licorice root tip, 12 parts of common selfheal fruit-spike, 9 parts of white mulberry root-bark, 7 parts of ash bark, 10 parts of tortoise-plastron gelatin, 20 parts of turtle shell gelatin, and 25 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, and xylitol, for subsequent use;

soaking: soaking the cleaned raw materials with 9 folds of water for 10 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decoction and concentrating with low heat, until a drug liquid does not disperse when being dropped on paper, to obtain a vegetarian paste;

collecting an oral paste: pouring xylitol, and melted turtle shell gelatin and tortoise-plastron gelatin into the vegetarian paste respectively, stirring them continuously with a shovel while cooking them slowly with low heat, until the juice can coagulate into beads and not disperse when being dropped into clear water, then canning the resulted oral paste.

In the above, the step of melting gelatin type drugs is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 4:

A Chinese herbal oral paste for conditioning dampness-heat constitution includes the following components in parts by weight: 13 parts of baical skullcap root, 13 parts of unprocessed rehmannia root, 13 parts of plantain seed, 24 parts of purslane herb, 13 parts of angelica, 4 parts of cardamon fruit, 15 parts of virgate wormwood herb, 18 parts of rice beans, 13 parts of weeping forsythia capsule, 13 parts of thunberg fritillary bulb, 25 parts of Chinese waxgourd peel, 7 parts of mint, 7 parts of dried tangerine peel, 15 parts of prepared atractylodes rhizome, 19 parts of waxgourd seed, 7 parts of common anemarrhena rhizome, 13 parts of amur cork-tree, 18 parts of golden buckwheat rhizome, 15 parts of fuling, 15 parts of Chinese yam, 13 parts of bitter apricot seed, 25 parts of coix seed, 13 parts of bamboo leaf, 18 parts of Chinese wolfberry root-bark, 8 parts of ural licorice root tip, 18 parts of common selfheal fruit-spike, 15 parts of white mulberry root-bark, 13 parts of ash bark, 20 parts of tortoise-plastron gelatin, 30 parts of turtle shell gelatin, and 35 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, and xylitol, for subsequent use;

soaking: soaking the cleaned raw materials with 9 folds of water for 12 h, with the water over the raw materials by 15 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin and tortoise-plastron gelatin into the vegetarian paste respectively, stirring them continuously with a shovel while cooking them slowly with low heat, until the juice can coagulate and not disperse into beads when being dropped into clear water, then canning the resulted oral paste.

In the above, the step of melting gelatin type drugs is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

Embodiment 5:

A Chinese herbal oral paste for conditioning dampness-heat constitution includes the following components in parts by weight: 10 parts of baical skullcap root, 10 parts of unprocessed rehmannia root, 10 parts of plantain seed, 20 parts of purslane herb, 10 parts of angelica, 3 parts of cardamon fruit, 12 parts of virgate wormwood herb, 15 parts of rice beans, 10 parts of weeping forsythia capsule, 10 parts of thunberg fritillary bulb, 20 parts of Chinese waxgourd peel, 6 parts of mint, 6 parts of dried tangerine peel, 12 parts of prepared atractylodes rhizome, 15 parts of waxgourd seed, 6 parts of common anemarrhena rhizome, 10 parts of amur cork-tree, 15 parts of golden buckwheat rhizome, 12 parts of fuling, 12 parts of Chinese yam, 10 parts of bitter apricot seed, 20 parts of coix seed, 10 parts of bamboo leaf, 15 parts of Chinese wolfberry root-bark, 6 parts of ural licorice root tip, 15 parts of common selfheal fruit-spike, 12 parts of white mulberry root-bark, 10 parts of ash bark, 15 parts of tortoise-plastron gelatin, 25 parts of turtle shell gelatin, and 30 parts of xylitol.

The processing method therefor includes the following steps in sequence:

preparation of materials: measuring raw materials of formula ratio according to composition of the Chinese herbal oral paste, and washing raw materials, except turtle shell gelatin, tortoise-plastron gelatin, and xylitol, for subsequent use;

soaking: soaking the cleaned raw materials with 9 folds of water for 11 h, with the water over the raw materials by 17 cm;

decoction: decocting the soaked drug materials over flame, firstly boiling the drug materials with high heat to sufficiently expand, then boiling the drug materials with low heat for 1.5 hours of decoction, then filtering drug juice with gauze, then soaking filtered dregs of decoction with clear water and decocting the soaked dregs of decoction with low heat for 1 hour, thus repeating 3 times, then combining the filtered drug juice, and squeezing and filtering the dregs to obtain squeezed juice; combining the decoction juice with the squeezed juice, followed by static settlement for 2 h, and filtering, to obtain a supernatant liquid for subsequent use;

concentration: boiling and skimming the supernatant liquid resulted in the decoction step, followed by stirring while decocting and concentrating with low heat, until a drug liquid does not disperse when being dropped on paper, to obtain a vegetarian paste;

collecting an oral paste: pouring xylitol, melted turtle shell gelatin and tortoise-plastron gelatin into the vegetarian paste respectively, stirring them continuously with a shovel and cooking them slowly with low heat, until the juice can coagulate into beads and not disperse when being dropped into clear water, then canning the resulted oral paste.

In the above, the step of melting gelatin type drugs is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

EXPERIMENT EXAMPLE 1

The Followings are a Test of Effects of the Chinese Herbal Oral Paste for Conditioning Dampness-heat Constitution Prepared According to Embodiment 5 of the Present Disclosure Basic conditions of cases: 300 clinical cases of dampness-heat constitution, including 150 male cases and 150 female cases.

Usage and dosage: 25 g each time, once a day. Brew 25 g of the oral paste with boiling water in a cup, and stir them to make the oral paste melt for administration.

Evaluation criteria for therapeutic effects:

Cured: clinical symptoms completely disappeared, and normal life was restored.

Effective: clinical symptoms partially disappeared, and various signs were gradually improved.

Ineffective: symptoms and signs were not obviously improved.

Result statistics: 228 cases cured, effective to 42 cases, and ineffective to 30 cases, i.e., effective to 270 cases in total, therefore the total effective rate was 90%.

EXPERIMENT EXAMPLE 2

Animal Experiment

Wistar rats were divided into 7 groups, 10 rats in each group, half male and half female, including control group, model group, and 5 experimental groups of Embodiments 1 to 5 of the present disclosure. In addition to the control group for normal diet in the normal environment, the remaining groups were subjected to modeling of damp-heat syndrome in accordance with *Chinese medicine experimental methodology* 1st Ed., the People's Health Press, pressed in May 2008. The specific modeling methods is high-sucrose and high-fat diet, climate (temperature of 35° C. and air relative humidity of 95%), *Salmonella typhimurium* (106/ml). The rats were fed with high-sucrose and high-fat diet for 10 days, and subsequently put into a modeling box at temperature of 35° C. with a relative humidity of 95%. After 96 h, *Salmonella typhimurium* was was applied in an amount of 2 ml/200 g (body weight) by gavage, and after 120 h, infection was enhanced once [1 ml/200 g (body weight)]. Thereafter, the rats were removed and placed in the natural environment. This is the model group of rats. Rats in normal group were fed with normal diet under normal environment.

The experimental group according to the present disclosure was given the Chinese herbal oral paste prepared in Embodiments 1 to 5 of the present disclosure. The Chinese herbal oral paste were administrated by gavage for one week at a dosage for rat of 0.4 g/rat/day, which was obtained after conversion from a dosage for human being of 24 g/60 kg body weight. After one week of administration, the artery blood was sampled and the rats were sacrificed. The Chinese herbal oral paste was tested for the effect on body weight and blood viscosity of the dampness-heat model rats. The experimental results are shown in Table 1. The Chinese herbal oral paste was tested for the effect on the SOD (superoxide dismutase) and MDA (malondialdehyde) expression in serum and skin of the dampness-heat model rats. The experimental results are shown in Table 2.

TABLE 1

Effect of the Chinese Herbal Oral Paste of the Present Disclosure on Body Weight and Blood Viscosity of the Dampness-heat Model Rats

| Group | Number | Body Weight | Blood Midst Shear Viscosity (mpa · s) (115 $s^{-1}$) |
|---|---|---|---|
| Control Group | 10 | 312 ± 8.7** | 3.44 ± 0.15** |
| Model Group | 10 | 229 ± 10.2## | 6.88 ± 0.33## |
| Embodiment 1 | 10 | 293 ± 13.0* | 4.50 ± 0.29** |
| Embodiment 2 | 10 | 299 ± 11.8* | 4.62 ± 0.35** |
| Embodiment 3 | 10 | 280 ± 10.6** | 4.00 ± 0.25** |
| Embodiment 4 | 10 | 285 ± 9.7* | 3.84 ± 0.19* |
| Embodiment 5 | 10 | 291 ± 11.4** | 4.08 ± 0.23** |

TABLE 2

Effect of the Chinese Herbal Oral Paste of the Present Disclosure on the SOD and MDA expression in Serum and Skin of the Dampness-heat Model Rats

| Group | Number | Blood SOD (nmol/ml) | Skin SOD (nmol/ml) | Blood MDA (nmol/ml) | Skin MDA (nmol/ml) |
|---|---|---|---|---|---|
| Control Group | 10 | 7.24 ± 1.32** | 1.36 ± 0.018** | 5.27 ± 0.35** | 0.69 ± 0.08** |
| Model Group | 10 | 3.13 ± 0.96## | 0.44 ± 0.009## | 7.94 ± 0.53## | 1.01 ± 0.05## |
| Embodiment 1 | 10 | 6.66 ± 1.17** | 0.79 ± 0.007** | 6.88 ± 0.47** | 0.88 ± 0.06** |
| Embodiment 2 | 10 | 6.24 ± 1.33* | 0.73 ± 0.011** | 6.72 ± 0.51** | 0.85 ± 0.04** |
| Embodiment 3 | 10 | 5.81 ± 0.75** | 0.88 ± 0.006* | 6.15 ± 0.39** | 0.80 ± 0.04** |
| Embodiment 4 | 10 | 5.43 ± 0.92** | 0.70 ± 0.007* | 5.92 ± 0.50* | 0.85 ± 0.08** |
| Embodiment 5 | 10 | 5.33 ± 0.79* | 0.89 ± 0.006** | 5.70 ± 0.44** | 0.77 ± 0.05** |

(Note: # compared with normal group ##p<0.01, #p<0.05; * compared with model group *p<0.01, **p<0.05)

As can be seen from Table 1, the Chinese herbal oral paste in the experimental groups of Embodiments 1 to 5 of the present disclosure can significantly increase the body weight of the model rats and lower the whole blood viscosity, and have significant differences compared with the model group (p<0.01, p<0.05).

As can be seen from Table 2, all of the prescriptions of Embodiments 1-5 of the present disclosure can significantly increase the concentration of SOD in blood and skin so as to enhance the antioxidant capacity of the body. Meanwhile, the MDA in blood and skin of the model rats at each dosage is substantially decreased, indicating a reduction of the body's degree of oxidation.

It should be indicated that Embodiments 1-5 of the present invention are merely some of the embodiments for implementing the technical solutions of the present invention, and should not be construed as the scope of protection of the present invention merely limited to the above five embodiments, and a person skilled in the art can make further improvements on the basis of the present invention without departing from the principle and spirit of the present invention.

For example, the components of the Chinese herbal oral paste of the present invention are not limited to those listed in respective embodiments, while other Chinese herbal medicines also can be added, to further perfecting the drug formulation of the Chinese herbal oral paste of the present invention.

For another example, in the process of the processing method for the Chinese herbal oral paste of the present invention, in the concentration step, when the drug juice is concentrated to the vegetarian paste, a wild jujube shell powder is added evenly with stirring. The wild jujube shell powder above is obtained by sufficiently smashing and grinding the wild jujube shell, with a particle size of 100-400 micrometers. The wild jujube shell powder has the main components of cellulose and lignin, has quite advanced pores in the powder particles, and is a natural drug carrier. When added to the Chinese herbal oral paste, the pores inside the wild jujube shell powder will be filled up with the drug components of the Chinese herbal oral paste. Since the cellulose and lignin cannot be digested or absorbed in vivo, they can be effective as sustained release, then a small part of the drug components stored in the wild jujube shell powder can be released continuously, so that the drug is present in the digestive system for an extended period of time. The phenomenon that the drug components are wasted as the digestive system cannot absorb a large amount of drug components within a short period of time will not occur. The wild jujube shell powder is added in an amount of 1%-3% of the gelatin type drugs, and should not be used in an excessive amount, because the excessive amount, on one hand, will deteriorate the form quality of the oral paste, and on the other hand, will increase the burdens of the intestines and stomach as it cannot be absorbed by the human body.

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A Chinese herbal oral paste for conditioning dampness-heat constitution, comprising the following components in parts by weight: 5-15 parts of baical skullcap root, 5-15 parts of unprocessed rehmannia root, 4-16 parts of plantain seed, 12-28 parts of purslane herb, 3-17 parts of angelica, 1-5 parts of cardamon fruit, 5-19 parts of virgate wormwood herb, 9-21 parts of rice beans, 5-15 parts of weeping forsythia capsule, 5-16 parts of thunberg fritillary bulb, 10-30 parts of Chinese waxgourd peel, 3-9 parts of mint, 2-9 parts of dried tangerine peel, 7-19 parts of prepared atractylodes rhizome, 8-22 parts of waxgourd seed, 2-9 parts of common anemarrhena rhizome, 4-16 parts of amur cork-tree, 8-23 parts of golden buckwheat rhizome, 7-18 parts of fuling, 6-18 parts of Chinese yam, 5-15 parts of bitter apricot seed, 11-27 parts of coix seed, 5-16 parts of bamboo leaf, 8-20 parts of Chinese wolfberry root-bark, 2-9 parts of ural licorice root tip, 9-22 parts of common selfheal fruit-spike, 6-18 parts of white mulberry root-bark, 5-17 parts of ash bark, 7-25 parts of tortoise-plastron gelatin, 15-35 parts of turtle shell gelatin, and 20-30 parts of xylitol.

2. The Chinese herbal oral paste for conditioning dampness-heat constitution of claim 1, wherein the baical skullcap root is 7-13 parts by weight, the unprocessed rehmannia root is 7-13 parts by weight, the plantain seed is 7-13 parts by weight, the purslane herb is 16-24 parts by weight, the angelica is 7-13 parts by weight, the cardamon fruit is 2-4 parts by weight, the virgate wormwood herb is 9-15 parts by weight, the rice beans is 12-18 parts by weight, the weeping forsythia capsule is 7-13 parts by weight, the thunberg fritillary bulb is 7-13 parts by weight, the Chinese waxgourd peel is 15-25 parts by weight, the mint is 5-7 parts by weight, the dried tangerine peel is 5-7 parts by weight, the prepared atractylodes rhizome is 9-15 parts by weight, the waxgourd seed is 11-19 parts by weight, the common anemarrhena rhizome is 4-7 parts by weight, the amur cork-tree is 7-13 parts by weight, the golden buckwheat rhizome is 12-18 parts by weight, the fuling is 9-15 parts by weight, the Chinese yam is 9-15 parts by weight, the bitter apricot seed is 7-13 parts by weight, the coix seed is 15-25 parts by weight, the bamboo leaf is 7-13 parts by weight, the Chinese wolfberry root-bark is 12-18 parts by weight, the ural licorice root tip is 4-8 parts by weight, the common selfheal fruit-spike is 12-18 parts by weight, the white mulberry root-bark is 9-15 parts by weight, the ash bark is 7-13 parts by weight, the tortoise-plastron gelatin is 10-20 parts by weight, the turtle shell gelatin is 20-30 parts by weight, and the xylitol is 25-30 parts by weight.

3. The Chinese herbal oral paste for conditioning dampness-heat constitution of claim 1, wherein the baical skullcap root is 10 parts by weight, the unprocessed rehmannia root is 10 parts by weight, the plantain seed is 10 parts by weight, the purslane herb is 20 parts by weight, the angelica is 10 parts by weight, the cardamon fruit is 3 parts by weight, the virgate wormwood herb is 12 parts by weight, the rice beans is 15 parts by weight, the weeping forsythia capsule is 10 parts by weight, the thunberg fritillary bulb is 10 parts by weight, the Chinese waxgourd peel is 20 parts by weight, the mint is 6 parts by weight, the dried tangerine peel is 6 parts by weight, the prepared atractylodes rhizome is 12 parts by weight, the waxgourd seed is 15 parts by weight, the common anemarrhena rhizome is 6 parts by weight, the amur cork-tree is 10 parts by weight, the golden buckwheat rhizome is 15 parts by weight, the fuling is 12 parts by weight, the Chinese yam is 10 parts by weight, the bitter apricot seed is 10 parts by weight, the coix seed is 20 parts by weight, the bamboo leaf is 10 parts by weight, the Chinese wolfberry root-bark is 15 parts by weight, the ural licorice root tip is 6 parts by weight, the common selfheal fruit-spike is 15 parts by weight, the white mulberry root-bark is 12 parts by weight, the ash bark is 10 parts by weight, the tortoise-plastron gelatin is 15 parts by weight, the turtle shell gelatin is 25 parts by weight, and the xylitol is 30 parts by weight.

4. A processing method for the Chinese herbal oral paste for conditioning dampness-heat constitution of claim 1, comprising the following steps in sequence: preparation of materials, soaking, decoction, concentration, and collecting an oral paste.

5. The processing method for the Chinese herbal oral paste for conditioning dampness-heat constitution of claim 4, wherein the step of preparation of materials is: measuring raw materials of formula ratio according to composition of the Chinese herbal oral paste, and washing raw materials, except turtle shell gelatin, tortoise-plastron gelatin, and xylitol, for subsequent use.

6. The processing method for the Chinese herbal oral paste for conditioning dampness-heat constitution of claim 5, wherein the soaking step is: soaking the cleaned raw materials with 8-10 folds of water for 8-15 h, with the water over the raw materials by 10-20 cm.

7. The processing method for the Chinese herbal oral paste for conditioning dampness-heat constitution of claim 6, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

8. The processing method for the Chinese herbal oral paste for conditioning dampness-heat constitution of claim 7, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

9. The processing method for the Chinese herbal oral paste for conditioning dampness-heat constitution of claim 8, wherein the step of collecting an oral paste is: pouring xylitol, and melted turtle shell gelatin and tortoise-plastron gelatin into the vegetarian paste respectively, stirring them continuously with a shovel while cooking them slowly with low heat, until the juice can coagulate into beads when being dropped into clear water and does not disperse, then canning the resulted oral paste.

10. The processing method for the Chinese herbal oral paste for conditioning dampness-heat constitution of claim 9, wherein the melting step is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

11. A processing method for the Chinese herbal oral paste for conditioning dampness-heat constitution of claim 2, comprising the following steps in sequence: preparation of materials, soaking, decoction, concentration, and collecting an oral paste.

12. The processing method for the Chinese herbal oral paste for conditioning dampness-heat constitution of claim 11, wherein the step of preparation of materials is: measuring raw materials of formula ratio according to composition of the Chinese herbal oral paste, and washing raw materials, except turtle shell gelatin, tortoise-plastron gelatin, and xylitol, for subsequent use.

13. The processing method for the Chinese herbal oral paste for conditioning dampness-heat constitution of claim 12, wherein the soaking step is: soaking the cleaned raw materials with 8-10 folds of water for 8-15 h, with the water over the raw materials by 10-20 cm.

14. The processing method for the Chinese herbal oral paste for conditioning dampness-heat constitution of claim 13, wherein the decoction step is: decocting the soaked drug materials over flame, firstly boiling the drug materials with high heat to sufficiently expand, then boiling the drug materials with low heat for 1-2 hours of decoction, then filtering drug juice with gauze, then soaking filtered dregs of decoction with clear water and decocting the soaked dregs of decoction with low heat for 1 hour, thus repeating 2-4 times, then combining the filtered drug juice, and squeezing and filtering the dregs to obtain a squeezed juice; combining the decoction juice with the squeezed juice, followed by static settlement for 2 h, and filtering, to obtain a supernatant liquid for subsequent use.

15. The processing method for the Chinese herbal oral paste for conditioning dampness-heat constitution of claim 14, wherein the concentration step is: boiling and skimming the supernatant liquid resulted in the decoction step, followed by stirring while decocting and concentrating with low heat, until a drug liquid does not disperse when being dropped on paper, to obtain a vegetarian paste.

16. The processing method for the Chinese herbal oral paste for conditioning dampness-heat constitution of claim 15, wherein the step of collecting an oral paste is: pouring xylitol, and melted turtle shell gelatin and tortoise-plastron gelatin into the vegetarian paste respectively, stirring them continuously with a shovel while cooking them slowly with low heat, until the juice can coagulate into beads when being dropped into clear water and does not disperse, then canning the resulted oral paste.

17. The processing method for the Chinese herbal oral paste for conditioning dampness-heat constitution of claim 16, wherein the melting step is: smashing lumps of turtle shell gelatin and tortoise-plastron gelatin into small gelatin pieces or gelatin powder, soaking and softening the small gelatin pieces or the gelatin powder in Shaoxing wine, water bath heating the softened small gelatin pieces or gelatin powder in a steamer until they are completely melted.

18. A processing method for the Chinese herbal oral paste for conditioning dampness-heat constitution of claim 3, comprising the following steps in sequence: preparation of materials, soaking, decoction, concentration, and collecting an oral paste.

19. The processing method for the Chinese herbal oral paste for conditioning dampness-heat constitution of claim 18, wherein the step of preparation of materials is: measuring raw materials of formula ratio according to composition of the Chinese herbal oral paste, and washing raw materials, except turtle shell gelatin, tortoise-plastron gelatin, and xylitol, for subsequent use.

20. The processing method for the Chinese herbal oral paste for conditioning dampness-heat constitution of claim 19, wherein the soaking step is: soaking the cleaned raw materials with 8-10 folds of water for 8-15 h, with the raw materials by 10-20 cm.

\* \* \* \* \*